United States Patent [19]

Stanley

[11] Patent Number: 6,099,834
[45] Date of Patent: Aug. 8, 2000

[54] METHOD FOR MODULATING EICOSANOID MEDIATED IMMUNE RESPONSES IN ARTHROPODS

[75] Inventor: David W. Stanley, Lincoln, Nebr.

[73] Assignee: Board of Regents University of Nebraska-Lincoln, Lincoln, Nebr.

[21] Appl. No.: 08/912,455

[22] Filed: Aug. 18, 1997

Related U.S. Application Data

[63] Continuation of application No. 08/371,471, Dec. 19, 1994, abandoned, which is a continuation of application No. 08/133,555, Oct. 7, 1993, abandoned, which is a continuation of application No. 07/825,671, Jan. 30, 1992, abandoned.

[51] Int. Cl.[7] ............................. A61K 38/43; A01N 43/42
[52] U.S. Cl. ..................... 424/94.1; 424/94.4; 424/94.5; 514/2; 514/12; 514/312; 435/183
[58] Field of Search .................................. 424/94.1, 94.3, 424/94.4, 94.5, 405, 184.1; 514/2, 12, 312, 425, 530, 560, 573, 885; 435/183

[56] References Cited

U.S. PATENT DOCUMENTS

| 4,153,705 | 5/1979 | Puttner et al. | 514/365 |
| 4,883,801 | 11/1989 | Nathanson | 514/263 |

OTHER PUBLICATIONS

Forgue et al Int. J. Immunopharmacol vol. 12 No. 2 p 155–163 issued 1990.

Stanley Samuelson et al. Proc. Natl. Acad. Sci. USA vol. 88 pp 1064–1068 Feb. 1, 1991.

PDR 41st Ed. Edward R. Barnhart Publisher Oradell N.J. 07649 pp 1274, 1895, 1463.

Wakayama et al. (1986). Insect Biochemistry 16: 903–910.

Rossetti et al. (1988) Jap. J. Physiol. 38: 179–186.

Massie et al. (1985) J. Gerontology 40: 257–260.

Author: Miller, et al., Title: Eicosanoids Mediate Nodulation Responses to Bacterial Infections in Larvae of the Tenebrionid Beetle, Zophobas atratus, Date: 1996, Pages: vol. 24, No. 1, pp. 3–12, Pub.: Journal of Insect Physiology.

Author: Miller, et al., Title: Eicosanoids Mediate Insect Nodulation Responses to Bacterial Infections, Date: Dec. 1994 Pages: vol. 91, pp. 12418–12422, Pub.: Proc. Natl. Acad. Sci. USA.

Author: Stanley–Samuelson, et al., Title: What can We Learn from Prostaglandins and Related Eicosanoids in Insects? Date: 1996, Pages: vol. 26, No. 3, pp. 223–234, Pub.: Insect Biochem. Molec. Biol.

Author: Stanley–Samuelson, Title: The Biological Significance of Prostaglandins and Related Eicosanoids in Invertebrates Date: 1994, Pages: vol. 34, pp. 589–598, Pub.: Amer. Zool.

D. Stanley Samuelson et al., "Evolutionary Aspects of Prostaglandins and Other Eicosanoids in Invertebrates", in Progress in Comparative Endocrinology, Wiley Liss Inc., at pp. 614–619 (1990).

D. Stanley Samuelson et al., "Insect Immune Responses to Bacterial Infection Is Mediated By Eicosanoids", Proc. Natl. Acad. Sci. USA, 88:1064–1068 (Feb. 1991).

J. Atkinson et al., in Handbook of Eicosanoids, Prostaglandins and Related Lipids, vol. 1B, A. Willie ed., CRC Press, Boca Raton, Florida, at pp. 175–263 (1989).

R. Bindra et al., in Prostaglandin Synthesis, Academic Press, New York, at pp. 291–330 (1977).

R. Bindra et al., in Prostaglandin Synthesis, Academic Press, New York, at pp. 337–348 (1977).

E. Corey et al., "Total Synthesis of Natural (levo) Enantiomeric (dextro) Forms of Prostaglandin $E_1$", J. Am. Chem. Soc., 91:536–536 (1969).

M. Fromm et al., "Expression of Genes Transferred Into Monocot and Dicot Plant Cells by Electroporation", PNAS, 82:5824–5829 (1984).

M. Hayashi et al., "Synthesis of 11–dehydro–13,14–dihydro–$PGE_1$ and $PGD_2$", J. Organ. Chem., 38:2115–2116 (1973).

R. Kelley et al., "Prostaglandin Synthesis: 1. An Improved Synthesis Through Bicyclo [3.1.0.] Hexane Intermediates", J. Am. Chem. Soc., 95:2746–2747 (1973).

Kirk–Othmer Concise Encyclopedia of Chemical Technology, 3rd edition, John Wiley & Sons, Prostaglandins at pp. 714–719 (1984).

T.M. Klein et al., "High Velocity Microprojectiles for Delivering Nucleic Acids Into Living Cells", Nature, 327:70–73 (1987).

P. Lurquin et al., "Binding of Large Liposomes to Plant Protoplast and Delivery of Encapsulated DNA", Plant Science Letters, 25:133–146 (1982).

C. McWhorter et al., "Adjuvants: A Guide to Terminology, Registered Uses, Selection and General Reference Works", Adjuvants for Herbicides, published by Weed Science Society of America, R. Hodgson, ed., at pp. 119–137 (1982).

(List continued on next page.)

Primary Examiner—Keith D. MacMillan
Assistant Examiner—P. Ponnaluri
Attorney, Agent, or Firm—Suiter & Associates PC

[57] ABSTRACT

The invention is directed to compositions which alter the health of invertebrate organisms by affecting eicosanoid-mediated immune responses, and methods of using the compositions. The invention provides pharmaceutical compositions and biopesticide compositions. The pharmaceutical composition is composed of an effective amount of at least one biologically active agent which enhances or inhibits eicosanoid-mediated immune responses in invertebrate species and a physiological compatible carrier. The biopesticide composition is composed of a biopesticidal amount of an inhibitor of eicosanoid-mediated immune responses in invertebrates and a physiologically acceptable carrier. The pharmaceutical compositions are useful to treat invertebrate species to enhance or inhibit immune responses. The biopesticide composition is useful to control the growth of or eradicate invertebrate pests. Methods are provided for determining which and what amounts of the biologically active agents are useful in the composition.

12 Claims, No Drawings

OTHER PUBLICATIONS

R. Newton, "Steric Control In Prostaglandin Synthesis Involving Bicyclic and Tricyclic Intermediates", *Tetrahedron*, 36:2163–2196 (1980).

R. Newton et al., "Strategies Employed in the Synthesis of Protocyclins and Thromboxanes", *Synthesis* at pp. 449–478 (1984).

N. Porter et al., "Prostaglandin $G_2$", *J. Am. Chem. Soc.*, 102:1183–1184 (1980).

B. Samuelsson, "Leukotrienes, Mediators of Immediate Hypersensitivity Reactions and Inflammation", *Science*, 220: 568–575 (1983).

Sih et al., "Asymmetric Total Synthesis of (–)–Prostaglandin $E_1$ and (–)–Prostaglandin $E_2$", *J. Am. Chem. Soc.*, 97:865–874 (1975).

D. White, "Prostaglandin Synthesis: Regio–Specific Generation of a Latent Mixed Acyloin Under Neutral Conditions", *Tetrahedron Lett.*, 21:1753–1756 (1976).

D. Anthony, "Status of Research on Biological Agents for the Control of Mosquitos", in *Fundamental and Applied Aspects of Invertebrate Pathogens*, Proceedings of the 4th International Colloquium of Invertebrate Pathology, at pp. 176–193 (1986).

N. Becker et al., "Application of Irradiated Bacterial Insecticides in an Integrated Mosquito Control Program in West Germany", in *Fundamental and Applied Aspects of Invertebrate Pathogens*, Proceedings of the Fourth International Colloquium of Invertebrate Pathology, at p. 559 (1986).

H. Boman et al., "Cell–Free Immunity in Insects", *Ann. Rev. Microbiol.*, 41:103–126 (1987).

H. Burges et al., "Current Status of the Use of Bacteria as Biocontrol Agents", in *Fundamental and Applied Aspects of Invertebrate Pathogens*, Proc. of the 4th International Colloquium of Invertebrate Pathology, pp. 514–517 (1986).

K. Cutler et al., "Compound Discovered That Destroys Insect Immune Systems", in *AgBiotechnology News*, p. 3 (May/Jun. 1991).

R. Faust, Nature of Pathogenic Process of *Bacillus thuringiensis*, in *Fundamental and Applied Aspects of Invertebrate Pathogens*, Proc. of the 4th International Colloquium of Invertebrate Pathology, pp. 91–129 (1986).

J. Jarosz et al., "Selective Inhibition of Cecropin–like Activity of Insect Immune Blood by Protease from American Foulbrood Scales", *J. Invert. Path.*, 56:143–149 (1990).

V. Miller, "Entomologist Finds Way to Halt Insect Immune Response", *CO–WY—NE–IA–SD* (May 13, 1991).

V. Miller, "UNL Scientists Direct Attack on Killer Tomato Worms", *Exploring Life's Frontiers*, p. 7 (Apr. 1991).

V. Miller, "Team Finds Way to Block Insects' Immune Response", *Research Nebraska*, pp. 8–9 (Mar. 1991).

C. Pant, "Ecology and Control of Vectors: Use of Biological Agents as a Component of Integrated Vector Control Programmes", in *Fundamental and Applied Aspects of Invertebrate Pathogens*, Proceedings of the 4th International Colloquium of Invertebrate Pathology, at pp. 501–509 (1986).

N. Ratcliffe, "Invertebrate Immunity—A Primer for the Non–Specialist", *Immun. Lett.*, 10:253–270 (1985).

B. Ruggeri, "The Identification of Several Prostaglandin Moieties in *Crassostrea Virginica* and *Mytilus Edulis* by Radioimmunoassay and High Performance Liquid Chromatography", *Prostaglandins Leukotrienes and Medicine*, 20:69–77 (1985).

A. Sparks, "Penaeid Bacterial Septicemia. Syn. Penaeid Vibriosis", in *Synopsis of Invertebrate Pathology: Exclusive of Insects*, Elsevier Science Publishers B.V., at pp. 197–199 (1985).

A. Undeen, "Biological Control of the Psychodidae, Ceratopogonidae, and Simulildae (Diptera), Including New Data on the Effect of *Bacillus thuringiensis* Var. *israelensis* on Simuliidae", in *Fundamental and Applied Aspects of Invertebrate Pathogens*, Proceedings of the 4th International Colloquium of Invertebrate Pathology, at pp. 143–153 (1986).

B. Salafsky et al., "Schistosoma Mansonia: A Comparison of Secreted Versus Non–Secreted Euicosanoids in Developing Schistosomulae in Adults", *Experimental Parasitology*, 64:361 (1987).

Fletcher et al., "Structure of the Mitogen–inducible TIS10 Gene and Demonstration That the TIS10–encoded protein is a Functional Prostaglandin G/H Synthase", *J. Biol. Chem.*, 267:4338 (1992).

Pawlowski et al., "Cloning and Sequencing of the cDNA for Rat Liver 3–alpha–Hydroxysteroid/Dihydrodiol Dehydrogenase", *J. Biol. Chem.*, 266:8820 (1991).

Funk et al., "Human Platelet/Erythroleukemia Cell Prostaglandin G/H Synthase: cDNA Cloning, Expression, and Gene Chromosomal Assignment", *FASEB Journal*, 5:2304 (1991).

Cheng et al., "Molecular Cloning and Expression of Rat Liver 3–alpha–Hydroxysteroid Dehydrogenase", *Mol. Endocrinology*, 5:823 (1991).

Watanabe et al., "Expression of Bovine Lung Prostaglandin F Synthase in *Escherichia coli*", *Biochem. and Biophys. Res. Comm.*, 181:272 (1991).

Seilhamer et al., "Pancreatic Phospholipase $A_2$: Isolation of the Human Gene and cDNAs from Porcine Pancreas and Human Lung", *DNA*, 5:519 (1986).

Ha et al., "Identification of Upstream Regulatory Elements Involved in the Developmental Expression of the *Arabidopsis thaliana* cabl Gene", *PNAS*, 85:8017 (1988).

Lam et al., "Site–specific Mutations Alter in vitro Factor Binding and Change Promoter Expression Pattern in Transgenic Plants", *PNAS*, 86:7890 (1989).

Channon et al., "A Calcium–dependent Mechanism for Associating a Soluble Arachiodonoyl–hydrolyzing Phospholipase $A_2$ with Membrane in the Macrophage Cell Line RAW 264.7", *J. Biol. Chem.*, 265:5409 (1990).

Ragab–Thomas et al., "Pathways of Arachiodonic Acid Liberation in Thrombin and Calcium Ionophore A23187–Stimulated Human Endothelial Cells: Respective Roles of Phospholipids and Triacylglycerol and Evidence for Diacyglycerol Generation from Phosphatidylcholine", *BBA*, 917:388 (1987).

Ragab et al., "Phospholipase $A_2$ Activity in Reproductive Tissues of the Firebrat *Thermobia Domestica* (Insecta: Thysanura)", *Insect Biochem. Molec. Biol.*, 22:379 (1992).

Ratcliffe, "Invertebrate Immunity—A Primer for the Non–Specialist", *Immunology Letters*, 10 at pp. 257–261 (1985).

Kirk–Othmer, *Encyclopedia of Chemical Technology*, Third Edition (Supplement Volume), John Wiley & Sons, publishers, at pp. 714–719.

METHOD FOR MODULATING EICOSANOID MEDIATED IMMUNE RESPONSES IN ARTHROPODS

This is a file-wrapper continuation of application Ser. No. 08/371,471 filed on Dec. 19, 1994, now abandoned which is a file wrapper continuation of application Ser. No. 08/133,555, filed Oct. 7, 1993, abandoned, which is a continuation of application Ser. No. 07/825,671, filed Jan. 30, 1992, abandoned.

BACKGROUND OF THE INVENTION

Invertebrates comprise 95% of all known species in the animal kingdom and include a vast diversity of animals from unicellular protozoans to the more complex echinoderms and protocordates. Many species of invertebrates are pests, especially the 750,000 known species of insects which compete with man for agricultural, forestal and animal products. Other invertebrate species act as vectors of diseases such as malaria and trypanosomiasis which affect more than one billion people. In contrast, some invertebrate species serve as food sources, such as mollusks and crustaceans, and are of commercial importance and, in some cases, commercially farmed. Thus, management of invertebrate species is important because of the impact of agriculture pests on the availability of food and other resources, the impact of vector born disease on human health, and the impact of disastrous outbreaks of disease in invertebrates of commercial importance.

One management strategy for control of invertebrate vectors of human or animal disease or agricultural pests involves the use of chemical pesticides. However, many pest species have never been successfully controlled with chemical pesticides. Moreover, some of the most effective chemical pesticides, like DDT, have been banned from use because of environmental and health concerns. Those pest species which have been successfully controlled or eradicated with chemical pesticides can become resistant to the chemical pesticides, necessitating the development of new chemical formulations. Although, chemical pesticides are still widely used, the problems of environmental contamination, risk to human health, and resistance represent serious drawbacks to relying solely on chemicals in the management of invertebrate pests.

The current management strategy of invertebrate pests involves integration of several different approaches including the use of biological control agents with or without the use of chemical pesticides. The biological control agents currently in use are either pathogens, parasites or predators (mostly larvivorous fish). A biological control agent used successfully is *Bacillus thurigiensis* which provides a toxin used to control growth of mosquitos, black flies, spruce bud worm, gypsy moth and lepidopterous pests. However, use of *Bacillus thurigiensis* and other infectious agents as pesticides represent less than 1% of the pesticide market. Biological pesticides have several drawbacks including higher cost, limited host range, low virulence, short shelf life, and difficulty in transportation. A better understanding of invertebrate immune defense mechanisms may contribute to optimal utilization of available biological pesticides and to the development of new biological control agents.

Management of commercially valuable invertebrate species is becoming more important as unfavorable conditions in aquacultures, commercial farms and the natural environment have led to an increase in fatal disease outbreaks. Unfavorable conditions include pollution of water and soils, crowded conditions that promote fighting and cannibalism and immobilization or capture of organisms which cause wounds. Commercial species of importance held in crowded conditions, like annelids, oysters, lobsters, penaeid shrimp, and soft-shelled crabs, can be decimated by infection with viruses, bacteria or fungi. Attempts to prevent these infections have not been described and an investigation of the immune response of these invertebrate species is essential to developing a strategy to prevent loss of these species both in nature and in the commercial farms.

Like vertebrate species, the immune system of invertebrates plays a central role in the resistance of the organisms to disease, however, little is known about invertebrate immune systems. It is known that invertebrates have both cellular and humoral components that can act in a coordinated way to provide protection from invading pathogens. Cellular responses mediated by hemocytes include phagocytosis, encapsulation, and various cytotoxic reactions such as release of lysozyme and activation of the prophenol oxidase system. These cellular responses are complimented by anti-bacterial action of lysozyme and anti-bacterial peptides known as the cecropins, attacins, diptericins and insect defensins. However, little is known about the early steps of the immune response as, for example, the transduction of foreign body invasion signals and subsequent initiation of early physiological defense responses. These early steps can be important in the eventual outcome of the infection, for example, an early immune response may prevent significant multiplication of a bacterial pathogen thereby preventing or delaying death of the host invertebrate.

Therefore it is an object of the present invention to identify steps in the invertebrate immune response, including early steps. It is also an object of the invention to develop compositions which can inhibit or stimulate the immune response in invertebrates. It is a further object of the invention to provide biopesticide compositions and methods of using these biopesticides to control growth of vectors of human disease and agricultural invertebrate pests. It is also an object of the invention to provide therapeutic compositions and methods of using therapeutic compositions to prevent fatal infections of invertebrate species of commercial value.

SUMMARY OF THE INVENTION

These and other goals are achieved by the present invention which is directed to a pharmaceutical composition which alters the health of invertebrate organisms by affecting the eicosanoid-mediated immune responses, and a method of using the composition. The pharmaceutical composition can be used in the treatment of invertebrates to enhance or to inhibit immunological responses. The invention also provides for a biopesticide composition and method of using the biopesticide to control or eradicate invertebrate pests. Methods are provided for determining which biologically active agents and what amounts are useful in the composition.

The pharmaceutical composition is an admixture of an effective immunoregulatory amount of at least one biologically active agent which modulates invertebrate eicosanoid-mediated immune responses and a physiological acceptable or biocompatible carrier. The biologically active agent can act to inhibit or enhance eicosanoid-mediated immune responses. An effective immunoregulatory amount is that amount of the biologically active agent which results in a change in the immune response. Agents which inhibit invertebrate eicosanoid biological activity can provide for an increase in susceptibility to disease and for an increase in mortality of the invertebrate species. Agents which enhance or stimulate invertebrate eicosanoid biological activity can provide for a decrease in susceptibility to disease and a decrease in mortality of the invertebrate species. The biologically active agent can also be one which acts primarily to modulate eicosanoid immune response without modifying or altering other invertebrate biological functions like reproductive function or water transport functions.

The invention provides for a method to determine whether and what amounts of the biologically active agent is effective to modulate eicosanoid-mediated immune responses in invertebrates useful in the pharmaceutical composition of the invention. An amount of the biologically active agent which modulates eicosanoid biosynthesis in a carrier is administered to an invertebrate species to yield a test population. The control population of the invertebrate species receives the carrier alone. Both the control and test populations are inoculated with an infectious agent and incubated for a sufficient time to allow for growth of the infectious agent. After incubation, tissue samples are withdrawn from test and control groups and plated on effective growth medium to provide for growth of infectious agent. The amount of the infectious agent recovered from the test population is compared to that of the control population. An increase or decrease in the amount of the infectious agent recovered from tissues from the test population in comparison with the amount recovered from the control tissue indicates whether and what amounts of biologically active agent administered to the invertebrate results in a change in the immune response.

Agents which can inhibit invertebrate eicosanoid-mediated immune responses can include antagonists of prostaglandins, leukotrienes and arachidonic acid, inhibitors of the enzymes of eicosanoid biosynthetic pathways, altered intermediates and/or altered enzymes of eicosanoid biosynthetic pathways, and inhibitors of signal molecules which turn on eicosanoid biosynthesis. Preferably, the biologically active agent is an inhibitor of the enzymes of the eicosanoid biosynthetic pathway, and more preferably the inhibitor is a peptide which blocks the active site of an enzyme in the eicosanoid biosynthetic pathway.

Agents which can enhance or stimulate invertebrate eicosanoid-mediated immune responses include prostaglandins, leukotrienes, arachidonic acid and analogs thereof, agents which stimulate the enzymes of eicosanoid biosynthetic pathways, altered enzymes of the eicosanoid biosynthetic pathway, inhibitors of inactivating enzymes like dehydrogenases and reductases, and agents which stimulate signal molecules which turn on eicosanoid biosynthesis. Preferably, the biologically active agent is an analog of a prostaglandin, leukotriene, or arachidonic acid and more preferably, an analog which is orally active, has prolonged duration of biological activity and increased potency when compared to naturally occurring eicosanoids.

The biologically active agent can also be a genetically engineered organism which, expresses, secretes and delivers an agent which alters eicosanoid-mediated immune responses. Suitable organisms can be genetically-engineered yeast, bacteria, viruses, plants or fungi. The organism is preferably a microorganism which can infect and grow in the particular invertebrate species and, more preferably, a pathogenic microorganism. Genes can be cloned and introduced into the organism by standard recombinant DNA methods and include genes encoding the enzymes of the eicosanoid biosynthetic pathway, genes encoding altered enzymes of the eicosanoid biosynthetic pathway, genes encoding altered signal transduction molecules, and genes encoding peptides which block the active site of the enzymes of the eicosanoid biosynthetic pathway. In a preferred version, a pathogenic bacteria like *Serratia marcescens*, is transformed with a plasmid containing a gene encoding a peptide which blocks or inhibits the active site of an enzyme of the eicosanoid biosynthetic pathway so that the pathogen expresses, secretes and delivers the peptide inhibitor to the target invertebrate species.

The biologically active agent is combined with a suitable carrier which functions to assist delivery of the agent to the appropriate site. The choice of carrier depends upon the habitat of the invertebrate, type of food consumed by the invertebrate, and the physical characteristics of the biologically active agent. The biologically active agent is substantially soluble or dispersible in the carrier and the carrier is physiologically acceptable or compatible with invertebrates, plants, fish and other vertebrate organisms. The carrier can function to help the biologically active agent adhere to plant leaves and other food sources consumed by the target invertebrate species. The carrier can also function to allow the biologically active agent to adhere and/or penetrate to the external skeletons, shells or cuticle of invertebrate species. The carrier can also be a food source for the invertebrate species. The carrier can be formulated into a liquid or powdered mixture for spray delivery, or as granules or liposomes. The carrier of the composition may further be comprised of a surface-active agent. The surface-active agent readily disperses in the carrier and increases the adherence and/or penetration of the carrier and biologically active agent to a target site.

The invention also provides for a biopesticide composition comprised of an effective pesticidal amount of at least one biologically active agent which inhibits eicosanoid-mediated immune responses of an invertebrate organism and a physiological acceptable carrier. An effective pesticidal amount is that amount of the biologically active agent which inhibits eicosanoid-mediated immune responses sufficiently to cause an increase in the mortality of the invertebrate organism. The effective pesticidal amount for a particular invertebrate species can be determined by a method provided for in the invention.

The biopesticide composition can further comprise a chemical or biological pesticide in one or a plurality of applications as dictated by the characteristics of the particular invertebrate species to be controlled or eradicated. The chemical or biological pesticides currently in use rarely result in total control or eradication of the invertebrate species. Resistant or surviving invertebrate larvae or adults simultaneously or subsequently exposed to a biological agent which inhibits eicosanoid biological activity can exhibit an inhibition of immune responses, an increase in susceptibility to infectious disease, and an increase in mortality. The biologically active agent can act together with other biological control agents, like *Bacillus thurigiensis*.

The invention also provides a method for altering the health of invertebrate animals by administering an effective immunoregulatory amount of a pharmaceutical composition containing a biologically active agent which modulates eicosanoid-mediated immune responses. An effective immunoregulatory amount is that amount of the biologically active agent which results in a change in the immune response. The pharmaceutical composition is administered by combining it with a food or water source and feeding it to the invertebrate species, by injecting, or preferably by spraying the composition onto the invertebrate and/or its food or water source. The composition can be formulated into a liquid, powder, granules, or sustained release and/or macro/micro capsules. The composition can further comprise antioxidants, UV protectants, and sustained release polymers.

A treatment method is provided wherein the biologically active agent is administered to an invertebrate species in an amount to decrease immune response capabilities making the invertebrate more susceptible to infectious disease and less likely to survive. A similar treatment method provides for administration of the biologically active agent in an effective amount to enhance immune response capabilities, making the organism less susceptible to infectious disease and more likely to survive an infectious disease challenge.

The invention also provides a method of controlling the growth of invertebrate pests by administering an effective pesticidal amount of a biopesticide composition to an invertebrate species until growth is effectively inhibited. The biopesticide composition is composed of at least one biologically active agent which inhibits eicosanoid-mediated immune responses and a physiological carrier. The composition is administered by combining it with a food or water source and feeding it to the invertebrate species, injecting, and preferably by spraying the biopesticide composition onto the invertebrate and/or its food and water source. An effective biopesticidal amount is that amount of the biologically active agent which inhibits the eicosanoid-mediated immune response sufficiently to cause an increase in the mortality of the invertebrate species. The composition is administered in a single or a plurality of applications until the growth of the invertebrate species is effectively inhibited.

DETAILED DESCRIPTION OF THE INVENTION

The pharmaceutical composition useful to alter the health of invertebrate organisms is formed by mixing an effective immunoregulatory amount of at least one biologically active agent which modulates eicosanoid-mediated immune responses and a physiologically acceptable or compatible carrier. The biologically active agent can act to inhibit or enhance eicosanoid-mediated immune responses. The agent is also preferably long-acting and orally active. An effective immunoregulatory amount of the biologically active agent which results in a change in the immune response of the invertebrate can be determined by the method provided in the present invention.

Agents which can inhibit eicosanoid biological activity include antagonists of prostaglandins, leukotrienes and arachidonic acid, altered intermediates or enzymes of eicosanoid biosynthetic pathways, inhibitors of signal molecules which turn on eicosanoid biosynthesis, and, preferably, inhibitors of the eicosanoid biosynthetic pathway. Agents which can enhance or stimulate invertebrate eicosanoid biological activity include agents which stimulate the enzymes of eicosanoid biosynthetic pathway, altered enzymes of the eicosanoid biosynthetic pathway, agents which stimulate signal molecules which turn on eicosanoid biosynthesis, inhibitors of eicosanoid inactivating enzymes like dehydrogenases and reductases, and preferably prostaglandins, leukotrienes, arachidonic acid and analogs thereof. Alternatively, the biologically active agent can be a genetically engineered organism, preferably an invertebrate pathogen, which expresses, secretes and delivers an agent which alters eicosanoid biological activity.

The biologically active agent is substantially soluble or dispersible in a suitable carrier which functions to assist delivery of the agent to the appropriate site. The carrier is physiologically acceptable or compatible with living organisms including invertebrates, plants, fish, and other vertebrates. The composition can further be comprised of a surface-active agent which increases adherence and/or penetration of the biologically active agent to the target site.

The pharmaceutical composition is administered in an effective immunoregulatory amount to an invertebrate organism by feeding by injecting or preferably by spraying the invertebrate species and/or its food or water source. An effective immunoregulatory amount is that amount of the biologically active agent which results in a change in the immune response. Accordingly, the composition can be used to treat invertebrate species to enhance or inhibit immune response capabilities of the organism.

The invention also provides a biopesticide formulation and method of using the biopesticide formulation to control or eradicate invertebrate pests. The biopesticide composition is comprised of an effective pesticidal amount of at least one biologically active agent which inhibits eicosanoid-mediated immune responses of an invertebrate organism and a physiological compatible carrier. An effective pesticidal amount is that amount of the biologically active agent which inhibits eicosanoid-mediate immune response sufficiently to cause an increase in the mortality of the invertebrate organism. Accordingly, the invention provides for a method of using the biopesticide composition to control the growth of or eradicate invertebrate pests.

Biologically Active Agents Which Modulate Invertebrate Eicosanoid-Mediated Immune Responses Biologically active agents useful in the invention can modulate eicosanoid-mediated immune responses in invertebrates. The role, if any, of eicosanoids in invertebrate immune responses was not previously known. The present invention has identified that eicosanoids mediate immune responses in invertebrates, including early immune responses, and provides for pharmaceutical and/or biopesticide compositions which can be used to modulate eicosanoid-mediated immune responses and alter the health of invertebrate species.

Eicosanoids are a family of biologically potent lipid acids. Examples of naturally occurring eicosanoids include prostaglandins E, F, A, B, C, D and derivatives thereof, leukotrienes $LTA_4$, $LTB_4$, $LTC_4$, $LTD_4$, and $LTE_4$ and derivatives thereof, and thromboxanes $A_2$ and $B_2$ and derivatives thereof. The compounds are biosynthetically produced in many species by enzymic conversion of polyunsaturated fatty acids. Chemical synthesis of eicosanoid and eicosanoid analogs are well known in the art. See, for example, the Corey synthesis described in E. Corey et al. *J. Am. Chem. Soc.*, 91:535 (1970), which is hereby incorporated by reference, which provides for the synthesis of naturally occurring $PGE_1$, $PGF_{1\alpha}$, and intermediates which are extensively used in the synthesis of prostaglandin analogs.

Other chemical syntheses of eicosanoids are reported in R. Kelley et al., *J. Am. Chem. Soc.*, 95:2746 (1973); D. White, *Tetrahedron Lett.*, 1753 (1976); R. Newton et al., *Tetrahedron*, 36:2163 (1980) (synthesis of prostaglandins); C. Sih et al., *J. Am. Chem. Soc.*, 97:865 (1975) (prostaglandin synthesis involving the 1,4 addition of an organometallic reagent to α-β unsaturated ketone function); M. Hayashi et al., *J. Org. Chem.*, 38:2115 (1973) (synthesis of prostaglandin $D_2$); R. Bindra et al., in *Prostaglandin Synthesis*, Academic Press, N.Y. at pages 291–330 ( )1977) (partial synthesis of prostaglandins A, B and C); N. Porter et al., *J. Am. Chem. Soc.*, 102:1183 (1980) (synthesis of prostaglandin endoperoxides $PGH_1$ and $PGH_2$); R. Newton et al., *Synthesis* at page 449 (1984) (synthesis of prostacyclins, PGIs, and thromboxanes); B. Samuelsson, *Science*, 220:568 (1983) and J. Atkinson et al., in *Handbook of Eicosanoids, Prostaglandins and Related Lipids*, Vol. 1B, A. Willie ed., CRC Press, Boca Raton, Fla., at pages 175–263 (1989) (synthesis of leukotrienes and biological activity); and R. Bindra et al. in *Prostaglandin Synthesis*, Academic Press, N.Y. at pages 337–348 (1977) (chemical interconversion of different prostaglandin families), which are hereby incorporated by reference.

Eicosanoid biosynthesis in vertebrate species has been described in Kirk-Othmer *Concise Encyclopedia of Chemical Technology*, 3rd edition, at pages 714 to 719 (1984), which is hereby incorporated by reference. Biosynthesis of eicosanoids begins with the conversion of unesterified polyunsaturated fatty acids to arachidonic acid. Unesterified polyunsaturated acids can be obtained from the diet or alternatively from membrane phospholipids by the action of phospholipases. Arachidonic acid can be converted via enzymatic activity of cyclooxygenase to unstable endoperoxides, such as $PGG_2$ and $PGH_2$, which can then be converted to prostaglandins and thromboxanes. Alternatively, arachidonic acid can be enzymatically converted by lipoxygenase enzyme activity to form leukotrienes. Although not meant to be a limitation of the invention, it is believed that eicosanoid biosynthesis in invertebrates occurs via similar enzymatic action as that of eicosanoid biosynthesis in vertebrate species.

Eicosanoid biosynthesis in invertebrates is known to occur as prostaglandins and hydroxyeicosatetraenoic acids are present in invertebrate tissues. Precursor polyunsaturated fatty acids, like omega-3 polyenoic acids, arachidonic acid, and eicosatrieneoic acids, are present in fatty acid and phospholipid populations of invertebrate species. Inhibitors of prostaglandin biosynthesis, like glucocorticoids and non-steroidal anti-inflammatory drugs, act to prevent prostaglandin biosynthesis in invertebrate tissues. More specifically, inhibitors of cyclooxygenase, like acetyl salicylic acid, indicate the presence of cyclooxygenase activity by inhibition of prostaglandin-mediated oviposition behavior in silk moths. Phospholipase inhibitors, like glucocorticoids, indicate the presence of phospholipase enzymatic activity by inhibition of the production of arachidonic acid from membrane phospholipid precursors. Inhibitors of lipoxygenase, like esculetin, indicate the presence of lipoxygenase enzymatic activity by inhibiting the eicosanoid-mediated host penetration behavior of the blood fluke *Schistosoma mansoni*.

In vertebrate species, eicosanoid biosynthesis is initiated by a membrane-mediated event, like phagocytosis or binding of an antigen to receptors, which can trigger an influx of calcium ions, a transient increase in cyclic adenosine monophosphate (cAMP), activation of phospholipases with cleavage of arachidonic acid from phospholipids, and conversion of arachidonic acid to prostaglandins and thromboxanes via cyclooxygenase catalyzed oxidation, and to leukotrienes via enzymatic action of a lipoxygenase in the cell. The newly synthesized prostaglandins, thromboxanes and leukotrienes can be secreted by the cell and act to mediate stimulation of chemotaxis, chemokinesis, phagocytosis, and adherence responses of neutrophils and macrophages. Although not meant to be a limitation on this invention, it is believed that initiation of eicosanoid biosynthesis in invertebrates could occur in a similar manner.

Little is known about the spectrum of biological activity of eicosanoids in invertebrate species. Eicosanoids have been identified in a wide variety of invertebrates including sponges, echinoderms, arthropods, mollusks, and rotifers. Eicosanoids can mediate egg-laying behavior in crickets, hatching of barnacles, egg production in snails, spawning behavior of abalone, spawning behavior of the Pacific oyster, osmoregulation and water transport in *Modiolus demissuss*, host skin penetration of blood flukes, and evasion of host defense mechanisms by *Schistosoma mansoni*. A more detailed description of these functions of eicosanoids in invertebrate species is provided by D. Stanley-Samuelson et al., in *Progress in Comparative Endocrinology*, Wiley Liss Inc., at pages 614–619 (1990), which is hereby incorporated by reference.

It was not previously known whether eicosanoids mediate immune responses in invertebrates. Invertebrate immune response systems are not well characterized and may function significantly differently from that of the vertebrate species. Although not meant to be a limitation of the invention, it is believed that eicosanoids mediate immune responses in invertebrates and provide for pharmaceutical and/or biopesticide compositions which can modulate eicosanoid-mediated immune responses.

The biologically active agents of the invention are those which modulate immunoregulatory eicosanoid biological activity in invertebrates. The biologically active agent which modulates immunoregulatory eicosanoid biological activity in invertebrates can be selected from the group of compounds known to modulate vertebrate eicosanoid biological activity and tested in invertebrates to determine whether and what amount of the biologically active agent modulates invertebrate immune responses. Alternatively, the biologically active compound can be a novel compound which modulates eicosanoid-mediated immune response in invertebrates. A modulation in the invertebrate immune response is determined in the method provided in the invention by detecting an increase or decrease in the growth of an infectious agent in the invertebrate species in comparison to untreated control population of the invertebrate species.

Agents which inhibit invertebrate eicosanoid-mediated immune responses can provide for an increase in susceptibility to disease and an increase in mortality. Agents which enhance or stimulate invertebrate eicosanoid-mediated immune responses can provide for a decrease in susceptibility to infectious disease and a decrease in mortality of the invertebrate species. The biologically active agent can also be one which acts primarily to modulate eicosanoid-mediated immune response without modifying or altering other biological functions of the invertebrate. The biologically active agent is preferably one which has long duration and is orally active.

An effective amount of the biologically active agent depends in part on the type of invertebrate species, the size of the invertebrate, the method of administration, and the type of biologically active agent. Routes of administration can include absorption of the agent through skin and exterior surfaces of the invertebrate species, ingestion of the agent through the mouth or gills including from a food or water source, and injecting the biologically active agent. The route of administration chosen will depend on the type of invertebrate species and the stage of the life cycle when the biologically active agent is administered. For example, when the compositions of the invention are administered to the larval stage, the route of administration is preferably by ingestion of the compositions of the invention in combination with food or water source. The compositions can also be administered to larvae by absorption through skin and exterior surfaces as many larvae soft external surfaces than the adult stage exoskeletons, cuticles, or shells. If the invertebrate is an adult crustacean, the compositions are preferably administered via ingestion including ingestion with a food source. The composition is preferably administered to agricultural pests by spraying the affected plants followed by ingestion of the plant tissues coated with the compositions of the invention. Methods of administration suitable for particular invertebrates are well known in the art, some of which are described in R. Samson in *Fundamental and Applied Aspects of Invertebrate Pathology*, Proceedings of Fourth International Colloquium of Invertebrate Pathology at pages 597–687, the disclosure of which is hereby incorporated by reference.

An effective amount for the particular invertebrate species is preferably that amount of the biologically active agent which results in a change in the immune response. The change in the immune response for a particular invertebrate species can be identified by an increase or decrease in susceptibility of the invertebrate species to an infectious agent and can be determined by the method provided in the invention. Preferably, dosages can range from about $1\times10^{-6}$ µg/gm body weight to $1\times10^{5}$ µg/gm body weight, and more preferably, about $1\times10^{-6}$ µg/gm body weight to $1\times10^{3}$ µg/gm body weight, and most preferably, about $1\times10^{-4}$ µg/gm body weight to 1 µg/gm body weight Examples of agents which modulate eicosanoid-mediated immune response are those which alter formation and/or biological activity of the eicosanoids. These agents include agents that affect signal molecules which turn on eicosanoid biosynthesis, agents which modify the eicosanoid biosynthesis and/or formation, and agents which modify eicosanoid biological action. Agents that affect signal molecules can include agents which modulate the levels of cAMP or $Ca^{+2}$ ions, or those which modulate the activity of the phospholipases and protein kinases. Agents which alter or modify eicosanoid formation or biosynthesis can include altered enzymes of eicosanoid biosynthetic pathways, altered intermediates of eicosanoid biosynthetic pathways, specific active site inhibitors of eicosanoid biosynthetic enzymes, and other competitive and non-competitive inhibitors of eicosanoid biosynthesis. Agents which modify eicosanoid biological action can include eicosanoid analogs, eicosanoid antagonists, eicosanoid agonists, inhibitors of inactivating enzymes like inhibitors of eicosanoid dehydrogenases and reductases, and agents which interfere with the release of eicosanoids from cells. The eicosanoid analogs can be modified to enhance selectivity for invertebrate immune responses. Eicosanoid analogs can also preferably be modified to have longer duration, to act orally, and to have increased potency over naturally occurring eicosanoids.

The biologically active agent can also be a genetically engineered organism which expresses, secretes and delivers a biologically active agent which alters or modulates eicosanoid-mediated immune response in invertebrates.

Biologically Active Agents Which Inhibit Eicosanoid-Mediated Immune Responses

Biologically active agents useful in the pharmaceutical and/or biopesticide compositions inhibit eicosanoid biological activity and provide for an inhibition of immune responses and an increase in susceptibility to disease. The inhibitors can also provide for an increase in mortality which can result from inability to clear an infection with opportunistic and other invertebrate pathogens, an inability to completely repair wounds, and an increase in susceptibility to cancer. The inhibitors can be modified to selectively modulate the immune responses. The inhibitors are preferably long-acting and orally active.

Inhibitors can include antagonists of prostaglandins, leukotrienes, and arachidonic acid, inhibitors of the enzymes of the eicosanoid biosynthetic pathway, altered intermediates or enzymes of eicosanoid biosynthetic pathways, inhibitors of release of prostaglandins, leukotrienes and thromboxanes from cells, and inhibitors of signal molecules which turn on eicosanoid biosynthesis. Preferably, the biologically active agent is an inhibitor of the enzymes of the biosynthetic pathway, and more preferably, the inhibitor is a peptide which blocks the active side of an enzyme in the eicosanoid biosynthetic pathway.

Examples of inhibitors of eicosanoid biosynthesis include cinnamic acid and derivatives thereof, arachidonic acid derivatives, glucocorticoids, dihydroxybenzopyran ketones and derivatives thereof, methanoleukotrienes and derivatives thereof, binapthalene derivatives, naphthalene acetic acid derivatives, phosphorylcholine derivatives, indole acetic acid derivatives, dihydropyridine carboxylic acid derivatives, phenanthrene carboxylic acids and derivatives thereof, salicylic acid acetate and derivatives thereof, neomycins, benzoxazoleacetic acids and derivatives thereof, and dihydroxyanthrone derivatives and mixtures thereof.

Specific examples of inhibitors of eicosanoid biosynthesis include inhibitors of the eicosanoid biosynthetic enzymes: phospholipase $A_2$, cyclooxygenase, 5-lipoxygenase, 12-lipoxygenase, and 15-lipoxygenase. Inhibitors of cyclooxygenase include Ebselen (2-phenyl-1,2-benzisoselenazol-3(2H)-one), curcumin, ETYA (5,8,11,14-eicosatetraynoic acid), naproxen, indomethacin, nonsteroidal anti-inflammatory drugs such as salicylic acid acetates and derivatives thereof, phenidone, benoxaprofen, and REV-5741. Inhibitors of phospholipase include phosphorylcholine and derivatives thereof, glucocorticoids, DEDA (7,7-dimethyl-eicosadienoic acid), neomycins and derivatives thereof, aminocephalosporanic acid and derivatives thereof, chlorpromazine HCl and derivatives thereof, dihydropyridine carboxylic acid and derivatives thereof, manoalide, phenanthrene carboxylic acids and derivatives thereof, and compound 48/80. Inhibitors of lipoxygenase enzymes include 5-lipoxygenase inhibitors: Ebselen, REV-5901 (2-[3(1-hydroxyhexyl)phenoxymethyl]quinoline hydrochloride), REV-5367, REV-5747, REV-5827, REV-5875, REV-5965, REV-6080, 12-lipoxygenase inhibitors: REV-5747, REV-5827, and REV-5901, 15-lipoxygenase inhibitors: REV-5367 and phenidone (1-phenyl-3-pyrazolidinone); and other lipoxygenase enzyme inhibitors including: anthralin, Baicalein (5,6,7-trihydroxyflavone), caffeic acid, curcumin, cinnamic acid and derivatives thereof, arachidonic acid derivatives, DEDA, dipyridamole, ETI (5,8,11-eicosatriynoic acid), esculetin, gossypol, indomethacin, NDGA (nordihydroguaiaretic acid), phenidone, benoxaprofen, methanoleukotrienes and derivatives thereof, AA-861 (2-(12-hydroxy-5,10-dodecadiynyl)-3,5,6-trimethyl-p-benzoquinone), nafazatrom, and quercetin.

Inhibitors can include antagonists and/or agonists of prostaglandins, leukotrienes and arachidonic acid. These inhibitors can prevent the biological action of eicosanoids by binding to receptors and active sites of enzymes and/or preventing release of eicosanoids from cells. Specific examples of these agents include the eicosanoid antagonists 13-APA (13-azaprostanoic acid), carbacyclin, $CTA_2$ (carbocyclic thromboxane A2 (CAS Registry No. 74034-56-3)), U-44069 (9,11-dideoxy-11-α-9-α-epoxymethanoprostaglandin F2α), U-46619 (cromolyn), DSCG ((15S)-15-hydroxy-11-α-9-α-(epoxymethano) prosta-5(Z),13(E)dienoic acid), oxatomide, $PTA_2$ (pinane thromboxane A2), xanthines and derivatives thereof, and mixtures thereof.

Inhibitors can include inhibitors of signal transduction molecules. Signal transduction molecules include calcium ions, phospholipases, cyclic AMP, and protein kinases. Specific examples of such inhibitors include A-3, erbstatin, genistein, H-7, K-252a, phloretin, sphingosine, staurosporin, calcium channel blockers, glucocorticoids, and mixtures thereof.

Altered intermediates of eicosanoid biosynthesis are analogs of prostaglandins, leukotrienes and thromboxanes which compete with naturally occurring eicosanoid intermediates and inhibit the biosynthetic enzyme activity, thereby inhibiting production of eicosanoids. Altered intermediates are not active and can be formed by a modification of the structure of eicosanoids, including modification of carbon-15, the carboxylic acid sidechain and the aliphatic sidechain of prostaglandins, $\beta$-$C_8$ sidechain of prostaglandins and thromboxanes, and the 2,6-diaxobicycloheptane skeleton of thromboxanes.

Altered enzymes of the eicosanoid biosynthetic pathway include derivatives of phospholipase $A_2$, cyclooxygenase, 5-lipoxygenase, 12-lipoxygenase, and 15-lipoxygenase. The altered enzymes which serve as inhibitors of eicosanoid-mediated immune response are inactive enzymatically and bind to the intermediates in eicosanoid biosynthesis. The altered enzymes compete with the naturally occurring enzymes by binding intermediates in the biosynthesis, but since the altered enzymes are enzymatically inactive, eicosanoid biosynthesis cannot proceed, thereby inhibiting production of eicosanoids. Altered enzymes which are inactive can be formed by modification of the amino acid sequence of the enzyme and preferably, the amino acid sequence of the active site of the particular eicosanoid biosynthetic enzyme is altered.

The biologically active agent which inhibits eicosanoid-mediated immune responses is substantially soluble or dispersible in the carrier. The inhibitor is combined with the carrier in an effective amount to form a pharmaceutical composition. The types of and effective amounts of the inhibitor are those agents and amounts which inhibit immune responses in the invertebrate species as determined by an increase in the growth of an infectious agent in the invertebrate species in comparison to the untreated control population.

Biologically Active Agents Which Enhance Eicosanoid Biological Activity

Biologically active agents which stimulate or enhance eicosanoid-mediated immune responses can provide for a decrease in the susceptibility to disease, including infectious disease. The stimulating agents can also provide for a decrease in the mortality. The stimulating agents can be modified to more selectively modulate immune responses. Preferably the stimulating agents are long-acting and orally active.

Agents which can enhance or stimulate invertebrate eicosanoid-mediated immune response include prostaglandins, leukotrienes, arachidonic acid and analogs thereof, agents which stimulate the enzyme of eicosanoid biosynthetic pathways, altered enzymes of the eicosanoid biosynthetic pathway, and agents which stimulate signal molecule which turn on eicosanoid biosynthesis. Preferably, the biologically active agent is an analog of a prostaglandin, leukotriene, or arachidonic acid, and more preferably an analog which is orally active, has prolonged duration of biological activity, and increased potency when compared with naturally occurring eicosanoids.

Specific examples of simulators of eicosanoid biosynthesis include omega group fatty acids, phospholipases and derivatives thereof, calcium ionophors, eicosanoid biosynthetic enzymes and derivatives thereof, eicosanoid biosynthetic intermediates, arachidonic acids and derivatives thereof, and mixtures thereof. Omega group fatty acids and arachidonic acid and derivatives thereof provide precursors for eicosanoid biosynthesis. Eicosanoid biosynthetic enzymes include phospholipases, cyclooxygenases, and lipoxygenases. Agents which provide signal molecules include phospholipases and calcium ionophors.

Altered biosynthetic enzymes are derivatives of phospholipase $A_2$, cyclooxygenase, 5-lipoxygenase, 12-lipoxygenase, and 15-lipoxygenase enzymes. The altered enzymes are enzymatically active and can function in eicosanoid biosynthetic pathways. Alterations can be made to the amino acid sequences of the enzyme and preferably alterations are made to the amino acid sequence of the active site of the eicosanoid biosynthetic enzymes.

Preferably the biologically active agent is an analog of prostaglandins, leukotrienes or arachidonic acid, and more preferably an analog which is orally active, has prolonged duration of biological activity, and increased potency in invertebrates. Analogs are formed by synthetic modification of the chemical structure of eicosanoids. Modifications to carbon-15, the carboxylic acid sidechain and the aliphatic sidechain of prostaglandins, the $\beta$-$C_8$ sidechain of prostaglandins and thromboxanes, and the 2,6-diaxobicycloheptane skeleton of thromboxanes can result in a longer-acting, orally active, and more potent analogs. Modification of eicosanoids at the sites can also provide an analog which acts substantially selectively to modulate invertebrate immune responses. Specific examples of longer-acting and orally active analogs of eicosanoids include 15(R)-15-methyl $PGE_2$, 11(R)-11-deoxy-11,16,16-trimethyl-$PGE_2$, dl-4,5-didehydro-16-phenoxy-17,18,19,20-tetranor-$PGE_2$ methyl ester, dl-(11R,15RS)-11,15-dihydroxy-15-methyl-9-oxo-13-thiaprostanoic acid p-benzamidophenylester, dl-(15RS)-15-deoxy-16-hydroxy-16-vinyl-$PGE_2$ methyl ester, and mixtures thereof.

The biologically active agent which stimulates eicosanoid-mediated immune responses is substantially soluble or dispersible in the carrier. The stimulating agent is combined with the carrier in an effective amount to form a pharmaceutical composition. The types and effective amounts of stimulating agents are those agents and amounts which enhance immune responses in the invertebrate species as determined by a decrease in the growth of an infectious agent in comparison to untreated control population.

The pharmaceutical composition is administered to invertebrate species to enhance immune responses and decrease susceptibility of the invertebrate to disease, including infectious disease. The stimulating agent can also provide a decrease in mortality by increasing resistance to infectious disease, enhancing wound repair, and increasing resistance to cancer. Accordingly, the pharmaceutical composition can be used in prophylaxis and treatment of disease, including infectious disease, in commercially important invertebrate species.

Biologically Active Agents Which Are Genetically Engineered Organisms

The biologically active agent can also be a genetically engineered organism which expresses, secretes and delivers an agent which alters or modulates eicosanoid-mediated immune responses to invertebrates. The agent which alters eicosanoid-mediated immune responses can be one that enhances or inhibits immune responses in invertebrates. For example, the agent may be a peptide which inhibits an active site of eicosanoid biosynthetic enzyme or an altered eicosanoid inactivating enzyme.

Suitable organisms include genetically engineered yeast, bacteria, viruses, plants or fungi. Preferably the organism is a microorganism which can infect and grow in the particular invertebrate species and, more preferably, a pathogenic microorganism. Genetically engineered pathogens of the invention can invade and produce disease in invertebrate species as well as deliver inhibitors of eicosanoid-mediated immune responses.

Genes can be cloned and introduced into the organisms by standard recombinant DNA methods. Such techniques are well known to those of skill in the art and are outlined in *Guide to Molecular Cloning Techniques: Methods in Enzymology,* Vol. 152, S. Berger and A. Kimal, ed., Academic Press, Inc., San Diego, Calif. (1987), which is hereby incorporated by reference. Genes can be introduced into cells by vector-mediated transformation with vectors like viruses and plasmids, or by physical methods of transformation including use of microprojectiles, microinjection, biolistic transformation, electroporation, incubation with calcium-precipitated DNA, and incubation with liposomes containing foreign DNA. See M. Fromm et al., *PNAS,* 82:5824 (1984) (electroporation); T. M. Klein et al., *Nature,* 327:70 (1987) (microprojectiles); P. Lurquin et al., *Plant Science Lett.,* 25:133 (1982) (liposomes), the disclosures of which are hereby incorporated by reference.

Genes which can be introduced into organisms as a single gene or a cassette containing multiple genes. For example, an expression cassette can include genes for selective markers like antibiotic resistance as well as genes encoding one or more biologically active agents which inhibit or enhance eicosanoid-mediated immune responses. Genes encoding the biologically active agents can be modified to provide for enhanced expression and/or secretion of the biologically active agent from the microorganism. Genes can also be hybrid genes with one DNA sequence encoding a transit peptide which allows for targeting and transport of the remainder of the molecule to the invertebrate target cell, and a second DNA sequence encoding at least one biologically active agent to be delivered to the invertebrate target cell.

Specific examples of genes which can be used to transform organisms, either alone or as a part of an expression cassette, include genes encoding eicosanoid biosynthetic enzymes and mutants thereof, genes encoding eicosanoid inactivating reductase and dehydrogenase enzymes and mutants thereof, genes encoding altered signal transduction molecules and mutants thereof, and genes encoding peptide inhibitors of the active sites of eicosanoid biosynthetic enzymes and mutants thereof.

In a preferred version, an invertebrate pathogenic agent, as for example, *Serratia marcescens,* is transformed with the gene encoding a peptide which blocks or inhibits the active site of an eicosanoid biosynthetic pathway enzyme. The pathogenic agent is transformed with a plasmid vector also containing a selectable marker or reporter gene. The transformed pathogen is selected using the selectable marker or reporter gene and expresses, secretes and delivers sufficient amount of the peptide inhibitor to the invertebrate species to provide an inhibition of the immune response.

The genetically transformed organism is substantially soluble or dispersible in the carrier. The genetically engineered organism is combined with the carrier in an effective amount to form a pharmaceutical and/or biopesticide composition. An effective amount of genetically engineered organism is that amount which alters or modulates the invertebrate species immune responses. A genetically engineered non-pathogenic organism which infects and grows, can deliver immunostimulating agents to commercially valuable invertebrate species. The preferred version provides for a genetically engineered pathogen which can serve as a biopesticide for a particular invertebrate pest.

Method for Determining Whether and What Amount of the Biologically Active Agent Is Effective to Modulate Immune Responses in Invertebrates The invention provides a method for determining whether and what amounts of the biologically active agent result in a change in immune responses of the particular invertebrate species. The method involves administering different dosages of the biologically active agent in the carrier to the particular invertebrate species followed by inoculation of the invertebrate with an effective amount of an infectious agent, preferably a pathogen. A control group of organisms receives the carrier alone followed by inoculation with the infectious agent. After an effective incubation period to provide for sufficient growth of the infectious agent, preferably about 0.5 hours to 10 hours post-infection and more preferably about 1–5 hours post-infection, tissue or hemolymph samples are withdrawn from the invertebrate organism, extracted in physiological solution, and incubated with growth medium. Suitable physiological solutions include physiological salt solutions of sodium chloride, sodium phosphate, and sodium citrate. The growth medium is incubated until sufficient growth of the infectious agent occurs, and the amount of infectious agent present in the sample is determined. A change in the immune response is determined by comparing the amount of infectious agent recovered from the tissue samples from the invertebrate organisms receiving different doses of the biologically active agent with the amount of infectious agents recovered from control organisms. An increase or decrease in the amount of infectious agent recovered from organisms treated with the biologically active agent, and preferably, an increase or decrease at least about 2-fold, indicates a change in the immune response. An effective immunoregulatory amount can be calculated by determining which dosages of the biologically active agent result in a change in the immune response.

In a preferred version, an invertebrate agricultural pest species, as for example *Manduca sexta,* is injected with different dosages of dexamethasone, an inhibitor of eicosanoid biosynthesis. The organism is then injected with a pathogenic agent for the particular invertebrate species, like, for example, *Serratia marcescens.* The control group receives absolute ethanol followed by inoculation with the pathogenic agent. After about 1 hour post-infection, hemolymph samples are withdrawn, extracted, diluted, and plated on standard method agar plates to provide for growth of the pathogenic agent. *Serratia marcescens* colonies are incubated for 40–48 hours to provide for sufficient bacterial growth. As the dosage of the inhibitor is increased, the amount of pathogenic agent recovered from the tissue is determined. The lower doses of the inhibitor resulting in about 2-fold increase in the amount of the recovered bacteria and higher doses result in at least about a 20-fold increase over the amount of bacteria recovered from the control. An increase of at least about 2-fold in the amount of the pathogenic agent recovered from tissue samples of invertebrates treated with the inhibitor indicates an inhibition in the immune response.

Infectious agents useful in the method are those which can infect and grow in a particular invertebrate species, and are preferably pathogenic microorganisms. Suitable infectious agents and effective amounts for a particular invertebrate species to be tested in the method are known to those of skill in the art and are outlined in A. Sparks in *Synopsis of Invertebrate Pathology,* Elsevier, at pages 133–382 (1985) and in R. Samson et al. in *Fundamental and Applied Aspects of Invertebrate Pathogens,* Proceedings of the Fourth International Colloquium of Invertebrate Pathology, at pages 1–362 (1986), the disclosures of which are hereby incorporated by reference. Appropriate growth medium and growth conditions to recover the infectious agent from the tissue samples of the invertebrate are known to those of skill in the art.

The dosage range of the biologically active agent administered in the method depends on the size of the invertebrate, the type of biologically active agent, and the method of administration. Preferably, different dosages ranging from about $1\times10^{-6}$ µg/gm body weight to $1\times10^{5}$ µg/gm body weight, and more preferably, about $1\times10^{-6}$ µg/gm body weight to $1\times10^{3}$ µg/gm body weight, and most preferably, about $1\times10^{-4}$ µg/gm body weight to 1 µg/gm body weight can be administered to the invertebrate species to determine whether and what amounts of the particular biologically active agent modulate eicosanoid-mediate immune responses in the particular invertebrate species.

Carriers

The biologically active agent is combined with a suitable carrier which functions to assist delivery of the agent to the appropriate site. The choice of carrier depends on the habitat of the invertebrate, type of food consumed by the invertebrate, and the physical characteristics of the biologically active agent. The biologically active agent is substantially soluble or dispersible in the carrier, and the carrier is substantially physiologically acceptable or compatible with invertebrates, plants, fish, and other vertebrate organisms. The carrier can function to help the biologically active agent adhere to plant leaves and other food sources consumed by the targeted invertebrate species. The carrier can also function to allow the biologically active agent to adhere and/or penetrate the external skeletons, tests, shells, or cuticles of invertebrate species. The carrier can also be a food source for the invertebrate species like plant leaves or brine shrimp.

The carrier can be formulated into a liquid or powder or granular mixture for spray delivery or micro encapsulated in liposomes and the like. For example, a pharmaceutical composition suitable for aerial spraying can include an effective amount of biologically agent mixed with dried quart sand and vegetable oil. Specific examples of suitable carriers include paraffin wax, lecithins, vegetable oil, saline solutions, salt solutions, absolute ethanol, corn grits, sand, phospholipids, sustained release polymers and mixtures thereof. In a preferred version, the biologically active agent is dissolved in absolute ethanol and mixed with soybean lecithin and paraffin wax.

Sustained release polymers are those polymers that can incorporate the biologically active agent of the invention and provide for controlled release or delivery of the biologically active agent. Sustained release polymers can be formulated to provide for micro or macro encapsulation of the biologically active agent. Examples of suitable sustained release polymers are hydrogels, acrylates, polylactides, polyacrylic acids, polyethylene glycols, polyglycolides, and polymers with leachable occluded substances and mixtures thereof.

The carrier of the composition can be further comprised of a surface active agent. The surface active agent readily disperses in the carrier and increases the adherence and/or penetration of the carrier and biologically active agent to a target site. Suitable surface active agents include anionic surface agents, cationic surface agents, nonionic surface agents, and ampholytic surface active agents.

Surface active agents are present in the carrier in amounts effective to decrease surface tension, increase wettability, increase adherence to the target site, and increase penetration of the biologically active agent. Specific examples of the surface active agents are provided in *Adjuvants for Herbicides,* published by Weed Science Society of America, R. Hodgson, ed., at Chapter 8, pp. 119–137 (1982), the disclosure of which is hereby incorporated by reference.

The carrier can also include additives that enhance stability of and absorption of the biologically active agents. Additives, such as antioxidants and UV protectants, increase stability of the biologically active agents exposure to sun and oxygen. Additives which can assist in absorption of the biologically active agents can include propylene glycol, glycerol, urea, sodium lauryl sulfate, sorbitan ethoxylates, oleic acid, n-methyl pyrrolidone, dimethyl sulfoxide and mixtures thereof.

Biopesticide Composition

Biologically active agents which inhibit eicosanoid-mediated immune responses of the present invention are capable of functioning as biological pesticides either alone or in combination with other pesticides. A pest management strategy can involve combining chemical pesticides, biological pesticides, and the biopesticide inhibitors of the present invention to provide for control eradication of target invertebrate species.

Agents which can inhibit invertebrate eicosanoid-mediated immune responses can include antagonists of prostaglandins, leukotriene, and arachidonic acid, inhibitors of the eicosanoid biosynthetic pathway, altered intermediates and/or altered enzymes of the eicosanoid biosynthetic pathways, and inhibitors of signal molecules which turn on eicosanoid biosynthesis. The inhibitor can be long-acting and orally active. Preferably, the biologically active agent is an inhibitor of the enzymes of the eicosanoid biosynthetic pathway, and more preferably, the inhibitor is a peptide which blocks the active site of an enzyme in the eicosanoid biosynthetic pathway.

The biologically active agent can also be a genetically engineered organism which expresses, secretes and delivers an agent which inhibits eicosanoid-mediated immune responses of the invertebrate species. Suitable organisms can be genetically engineered yeast, bacteria, viruses, plants, or fungi. The organism is preferably a microorganism which can infect and grow in the particular invertebrate species and more preferably a microorganism or pathogenic microorganism. Genes are cloned and introduced into the organism by standard recombinant DNA methods and include genes encoding the enzyme of the eicosanoid biosynthetic pathway and mutants thereof, genes encoding altered signal transduction molecules and mutants thereof, and genes encoding peptides which block the active sites of the enzymes of the eicosanoid biosynthetic pathway. In a preferred version, a pathogenic bacteria, like *Serratia marcescens*, is transformed with a plasmid containing a gene encoding a peptide which blocks or inhibits the active site of an enzyme of the eicosanoid biosynthetic pathway, like phospholipase $A_2$.

An effective pesticidal amount of the biologically active agent depends in part on the invertebrate species, the size of the invertebrate, the method of administration, and the type of biologically active agent. An effective biopesticidal amount is that amount of the inhibitor which sufficiently inhibits eicosanoid-mediated immune response in the invertebrate to provide an increase in mortality of the invertebrate species and can be determined by the method of the invention. Suitable dosage ranges can include about $1 \times 10^{-6}$ μg/gm body weight to $1 \times 10^5$ μg/gm body weight, and more preferably, about $1 \times 10^{-6}$ μg/gm body weight to $1 \times 10^3$ μg/gm body weight, and most preferably, about $1 \times 10^{-4}$ μg/gm body weight to 1 μg/gm body weight. The invention also provides a method for determining which biologically active agents and what amounts are effective to control the growth of the particular invertebrate species.

The biologically active agent is combined with a suitable carrier which functions to assist delivery of the agent to the appropriate site. The choice of carrier depends on the habitat of the invertebrate, type of food consumed by the invertebrate, and the physical characteristics of the biologically active agent. The biologically active agent is substantially soluble or dispersible in the carrier, and the carrier is substantially physiologically acceptable or compatible with invertebrates, plants, fish, and other vertebrate organisms. The carrier can function to help the biologically active agent adhere to plant leaves and other food sources consumed by the targeted invertebrate species. The carrier can also function to allow the biologically active agent to adhere and/or penetrate the external skeletons, tests, shells, or cuticles of invertebrate species. The carrier can also be a food source for the invertebrate species like plant leaves or brine shrimp.

The carrier can be formulated into a liquid or powder or granular mixture for spray delivery or micro or macro capsules. Suitable carriers include paraffin wax; lecithins, vegetable oil, saline solutions, physiological salt solutions, absolute ethanol, corn grits, sand, membrane phospholipids, sustained release polymers, and mixtures thereof.

The biopesticide composition can further be comprised of additional agents which provide for stability and protection of biologically active agents from environmental conditions, like sun and oxygen. Suitable agents include UV protectants and antioxidants. The biopesticide composition can also be comprised of a surface active agent which aids in adherence and/or penetration of the biologically active agent. Suitable surface active agents include anionic surface agents, cationic surface agents, nonionic surface agents, and ampholytic surface agents.

Known chemical pesticides are useful in combination with the biopesticide compositions of the present invention to control or eradicate invertebrate species. Chemical pesticides are non-naturally occurring chemicals which can non-specifically kill invertebrate species at all stages of their life cycle. Chemical pesticides can persist in the environment and their effects are long-lasting. However, chemical pesticides are often not 100% effective and resistant species of invertebrates can arise. While not limiting the scope of the invention, it is believed that combining a chemical pesticide with the biological pesticide inhibitors of the present invention can improve efficacy of the chemical pesticide and eliminate resistant species, allowing for the use of lower doses of chemical pesticides. Specific examples of pesticides currently used in invertebrate pest control are DDT, malathion, fenitrothion, pirimiphosmethyl, carbamates, propoxur, bendiocarb, chlorphoxim, pryethroids, permethrin, deltamethrin, and temephos.

Known biological pesticides are useful in combination with the biopesticide compositions of the present invention. Biological pesticides consist of naturally occurring organisms which are host specific and are biodegradable and, thereby, minimize the environmental contamination. Biological pesticides currently in use include invertebrate pathogens, parasites, and predators like larvivorus fish. Biological pesticides are also not 100% effective against invertebrate species, in part because of low virulence and limited host range. Although not meant to be a limitation of the scope of the invention, it is believed that combining known biological pesticides with the biopesticide inhibitors of the present invention may help to increase virulence and host range by allowing pathogens and parasites to grow more rapidly in invertebrate species while immune responses of the invertebrate species are inhibited. Examples of known biological control agents include species of *Bacillus thuringiensis, Bacillus popilliae, Bacillus sphaericus,* species of Nosema, *Serratia entomophila, Verticillium lecanii, Hirsutilla thompsonii, Metarhizum anisopliae,* and *Blauvaria bassiana.*

Inhibitors of eicosanoid-mediated immune responses useful as biopesticides can be combined with one or more chemical or biological pesticides in a carrier to form a biological pesticide composition. The biopesticide inhibitors are compatible with the biological or chemical pesticide and are substantially soluble or dispersible in the mixture of carrier and chemical or biological pesticide. The biopesticide inhibitors are present in the composition in an amount effective to inhibit the immune responses and provide an increase in the mortality of the target invertebrate species. The composition can be administered by spraying, injecting, painting, brushing, or squirting in a single or plurality of applications until the targeted invertebrate pest is controlled or eradicated.

In a preferred version, an effective biopesticidal amount of the inhibitor of eicosanoid biosynthesis, like dexamethasone, can be combined with a known biological pesticide, like *Bacillus thuringiensis* serotype H-14, by mixing with a carrier of paraffin wax and soybean lecithin. This composition can be administered by spraying to invertebrate pests, like mosquito larvae, of *Culex pipiens, Aedes vexans, Aedes cantans,* and *Anopheles maculipennis* until sufficient control or eradication of the invertebrate species is observed.

Method for Determining Whether and What Amounts of the Inhibitors of Eicosanoid-Mediated Immune Responses Are Useful in the Biopesticide Compositions The invention provides a method for determining whether and what amounts of the biologically active inhibitors result in an inhibition of the immune response sufficient to increase the mortality of the invertebrate species in response to a pathogenic infection. The method involves administering an amount of the biologically active inhibitor of eicosanoid-mediated immune responses in the carrier to the particular invertebrate species followed by inoculation of the invertebrate with an effective amount of an infectious agent, preferably a pathogen, to form a test population. A control population of organisms receives the carrier alone followed by inoculation with the infectious agent. The control and test populations are incubated for an effective period of time to provide for sufficient growth of the infectious agent, preferably about 5 to 72 hours post-infection, and more preferably about 5 to 24 hours post-infection. After the incubation, the percentage of organisms surviving in the test population is compared to the percentage of organisms surviving in the control group. A decrease in the percentage of organisms surviving of at least about 2-fold when compared with the control population over the same period of time indicates whether and what amount of the inhibitor inhibits invertebrate immune responses sufficiently to provide an increase in mortality. The effective biopesticidal amount of the inhibitor is calculated by determining which dosages of biologically active inhibitors result in an increase in mortality.

In a preferred version, an invertebrate agricultural pest, as for example *Manduca sexta,* is injected with different dosages of an inhibitor of eicosanoid biosynthesis, like dexamethasone. The invertebrate organism is injected with a pathogenic agent for the particular invertebrate species, like, for example, *Serratia marcescens*. The control group receives absolute ethanol followed by inoculation with a pathogenic agent. After about 14 hours post-infection, the number of surviving invertebrate organisms is counted. As the dosage of the inhibitor is increased, the percentage of surviving organisms decreases. The lower doses of the inhibitor result in about a 2-fold decrease in the percentage of organisms surviving and higher doses result in a 4-fold decrease in the percentage of organisms surviving the pathogenic infection. A decrease of at least about 2-fold in the percentage of organisms surviving the pathogenic infection indicates an inhibition of the immune response sufficient to increase mortality of the invertebrate species.

Infectious agents useful in the method are those which can infect and grow in a particular invertebrate species, and are preferably pathogenic microorganisms. Suitable infectious agents and effective amounts for a particular invertebrate species to be tested in the method are known to those of skill in the art and are outlined in A. Sparks in *Synopsis of Invertebrate Pathology*, Elsevier, at pages 133–382 (1985) and in R. Samson et al. in *Fundamental and Applied Aspects of Invertebrate Pathogens*, Proceedings of the Fourth International Colloquium of Invertebrate Pathology, at pages 1–362 (1986), the disclosures of which are hereby incorporated by reference.

The dosage range of the biologically active agent administered in the method depends on the size of the invertebrate, the type of biologically active agent, and the method of administration. Preferably, different dosages ranging from about $1 \times 10^{-6}$ $\mu$g/gm body weight to $1 \times 10^5$ $\mu$g/gm body weight, and more preferably, about $1 \times 10^{-6}$ $\mu$g/gm body weight to $1 \times 10^3$ $\mu$g/gm body weight, and most preferably, about $1 \times 10^{-4}$ $\mu$g/gm body weight to 1 $\mu$g/gm body weight can be administered to the invertebrate species to determine whether and what amounts of the biologically active agent modulate eicosanoid-mediated immune responses sufficiently to provide an increase in mortality and thus are useful in a biopesticide composition for a particular invertebrate species.

Method for Altering the Health of Invertebrate Animals With the Compositions Containing Biologically Active Agents Which Modulate Eicosanoid-Mediated Immune Responses The present invention also provides for a method for altering the health of invertebrate animals involving administering an effective immunoregulatory amount of a composition containing a biologically active agent which modulates eicosanoid-mediated immune responses. The biologically active agent can inhibit or enhance immune responses of invertebrates. The choice of the biologically active agent will depend on the goal of the treatment. If the goal of the treatment is to inhibit the growth of the invertebrate species, at least one inhibitor of eicosanoid-mediated immune responses can be included in the composition. If the goal is to protect invertebrate species from injurious conditions, at least one enhancer or stimulator of eicosanoid-mediated immune responses can be included in the composition.

An effective amount of the biologically active agent depends, in part, on the type of invertebrate species, the size of the invertebrate, the method of administration, and the type of biologically active agent. The route of administration chosen will depend on the type of invertebrate species and the stage of the life cycle when the biologically active agent is administered. For example, when the compositions of the invention are administered to the larval stage, the route of administration is preferably by ingestion of the compositions of the invention in combination with food or water source. The compositions can also be administered to larvae by absorption through skin and exterior surfaces as many larvae lack external exoskeletons, shells or cuticles. If the invertebrate is an adult crustacean, the compositions are preferably administered via ingestion including ingestion with a food source. The composition is preferably administered to agricultural pests by spraying affected plants followed by ingestion of the plant tissues coated with the compositions of the invention by the invertebrate pest. Methods of administration suitable for particular invertebrates are well known in the art, some of which are described in R. Samson in *Fundamental and Applied Aspects of Invertebrate Pathology*, Proceedings of Fourth International Colloquium of Invertebrate Pathology at pages 597–687, the disclosure of which is hereby incorporated by reference.

An effective amount for the particular invertebrate species is preferably that amount of the biologically active agent which results in a change in the immune response. A change in the immune response can be identified by an increase or decrease in the susceptibility of an invertebrate species to an infectious agent and can be determined by the method of the invention. Suitable dosage ranges include about $1 \times 10^{-6}$ $\mu$g/gm body weight to $1 \times 10^5$ $\mu$g/gm body weight, and more preferably, about $1 \times 10^{-6}$ $\mu$g/gm body weight to $1 \times 10^3$ $\mu$g/gm body weight, and more preferably, about $1 \times 10^{-4}$ $\mu$g/gm body weight to 1 $\mu$g/gm body weight.

The composition is administered by combining it with a food or water source and feeding it to the invertebrate species, by injection, or preferably by spraying the composition onto the invertebrate and/or its food or water source. The composition can be administered as a liquid, powder, granules, or encapsulated like, for example, in liposomes. The composition may be sprayed onto plant leaves and foliage or water sources by a low-pressure backpack sprayer, or by aerial spraying. The composition is delivered to the target invertebrate species by ingestion, including ingestion of a food or water source containing the biologically active agent, by penetration through the outer surface of the invertebrate body including wound penetration, and by injection. The composition can also be delivered by genetically engineered microorganism which, as it grows in the invertebrate species, expresses, secretes and delivers the biologically active agent. The composition can be administered at all stages if the life cycle of the invertebrate species, but is preferably administered to the larval stage. The composition can be administered as a single application or a plurality of applications until the goal of the treatment is achieved.

When the invertebrate species is an important food source of commercial value, like mollusks or crustaceans, the invention also provides a treatment method useful to protect the species from injurious conditions and/or treat disease of the species. The method involves administering a pharmaceutical composition containing an enhancer or stimulator of eicosanoid-mediated immune response in an amount effective to enhance immune responses. The enhanced immune response can be accompanied by an increase in the resistance of the invertebrate to injurious conditions, like infectious disease, and a decrease in mortality. The composition can be administered as granules or combined with a food source, such as brine shrimp, in a single or a plurality of applications until treatment is completed.

The method can also include administering the stimulating agents of the present invention along with known antiviral, antibacterial or antifungal agents. Suitable antibacterial agents include penicillins, cephalosporins, vancomycin, bacitracin, and other antibiotics. Suitable antiviral agents include vidarabine, acyclovir, ribavirin, amantadine hydrochloride, interferons, and the like. Suitable antifungal agents include nystatin, gentamicin, miconazole, and the like.

In a preferred version, an orally active and longer-acting analog of a prostaglandin is combined with a food source and administered to an aquaculture of a crustacean, like penaeid shrimp. The composition can be administered upon the first signs of infectious disease or as a prophylactic measure in a single or in multiple applications.

Method for Controlling the Growth of Invertebrate Pests

The present invention also provides a method for controlling or eradicating the growth of invertebrate pests involving administering an effective pesticidal amount of a biopesticide composition until growth of the invertebrate species is effectively inhibited. The biopesticide composition is composed of at least one biologically active agent which inhibits eicosanoid-mediated immune responses and a physiological compatible carrier. The choice of the biologically active agent will depend on the habitat and type of the invertebrate species. Suitable biologically active agents include those which inhibit eicosanoid-mediated immune responses sufficiently to result in an increase in mortality of the invertebrate species and can be determined by the method of the invention.

An effective biopesticidal amount of the biologically active agent depends on the type of invertebrate species, the size of the invertebrate, the method of administration, and the type of biologically active agent. An effective biopesticidal amount for the particular invertebrate species is preferably that amount of the biologically active inhibitor which inhibits immune responses sufficiently to result in a decrease of at least about 2-fold in the percentage of invertebrate organisms surviving a pathogenic infection when compared to control invertebrates. Suitable dosage ranges include about $1 \times 10^{-6}$ μg/gm body weight to $1 \times 10^5$ μg/gm body weight, and more preferably, about $1 \times 10^{-6}$ μg/gm body weight to $1 \times 10^3$ μg/gm body weight, and most preferably, about $1 \times 10^{-4}$ μg/gm body weight to 1 μg/gm body weight.

The composition is administered by combining it with a food or water source and feeding it to the invertebrate species, by injection, or preferably by spraying the composition onto the invertebrate and/or its food or water source. The composition can be administered as a liquid, powder, granules, or encapsulated like, for example, in liposomes. The composition may be sprayed onto plant leaves and foliage or water sources by a low-pressure backpack sprayer, or by aerial spraying. The composition is delivered to the target invertebrate species by ingestion, including ingestion of a food or water source containing the biologically active agent, by penetration through the outer surface of the invertebrate body including wound penetration, and by injection. The composition can also be delivered by genetically engineering microorganism which, as it grows in the invertebrate species, expresses, secretes and delivers the biologically active agent. The composition can be administered at all stages if the life cycle of the invertebrate species, but is preferably administered to the larval stage.

The biopesticidal composition is administered in a single or a plurality of applications until the growth of the invertebrate species is effectively inhibited. Inhibition of growth of the invertebrate species is determined by the percentage of invertebrate surviving after the administration of the composition. An effective inhibition of growth is about 50% to 100% of the invertebrate organisms dead, and preferably, 80% to 100% of the organisms dead, and most preferably, 95% to 100% of the organisms dead after administration of the biopesticide composition.

In a preferred version, an invertebrate pest species, like *Manducca sexta*, is sprayed in the field with a biopesticidal composition containing about 50 μg/ml body weight of an inhibitor of an eicosanoid biosynthetic enzyme in a carrier of paraffin wax and soybean lecithin. The biopesticide composition is applied until about 95% of the invertebrate pest is killed.

The invention has been described with reference to various specific and preferred embodiments and techniques, however, it should be understood that many variations and modifications may be made while remaining within the spirit and scope of the invention.

EXAMPLE 1

Larval tobacco hornworms, *Manduca sexta*, were reared under standard culture conditions at 28° C. under 16-hour light/8-hour dark photoperiod. Experiments used early fifth instar prewandering larvae. Test larvae were injected with 50 μg of either the phospholipase $A_2$ inhibitor dexamethasone [(11β, 16α)-9-fluoro-11,17,21-trihydroxy-16-methylpregna-1,4-diene-3,20-dione], the cyclooxygenase inhibitor indomethacin [1-(ρ-chlorobenzoyl)-5-methoxy-2-methyl-3-indolyl-acetic acid], the 5- and 12-lipoxygenase inhibitor esculetin (6,7-dihydroxycoumarin) the nonspecific antioxidant maleic acid (cis-butenedioic acid), or a 1:1 combination of indomethacin and esculetin in 5 μl ethanol. Control larvae were injected with 5 μl of absolute ethanol. Injections were made by inserting the needle of a Hamilton 701 syringe dorsolaterally above the last two spiracles, moving the needle into the hemocell parallel to the body wall to avoid injuring the alimentary canal, then depressing the plunger.

Three to 10 minutes after injection of inhibitors, larvae were infected with the pathogen *Serratia marcescens* by intrahemocoelic injection of about $5 \times 10^5$ bacterial cells in 10 μl of broth, on the opposite side in the manner described above. After a 2.5 hour incubation at 30° C., 100 μl of hemolymph was withdrawn from each insect. The hemolymph was diluted and plated on standard methods agar. The plates were allowed to dry, inverted and then incubated at 30° C. for 36–40 hours. Red bacterial colonies on each plate were then counted. In all bacterial recovery experiments, each agar plate represented a hemolymph sample withdrawn from individually identifiable larvae.

Bacteria were recovered from significantly more larvae treated with eicosanoid biosynthesis inhibitors than from control larvae. *S. marcescens* bacterial colonies were seen on 87% of the plates from dexamethasone treated larvae, whereas only 21% of the plates from control larvae had visible colonies. Larvae treated with compounds that block only one of the two main polyunsaturated fatty acid oxygenation pathways yielded intermediate results: colonies were recovered from about 58% of the esculetin-treated larvae, and from about 55% of the indomethacin-treated larvae. When both major pathways were inhibited simultaneously with indomethacin and esculetin, bacterial colonies were recovered from 86% of the larvae, which is nearly identical to the dexamethasone effect. Experiments with a nonspecific anti-oxidant compound maleic acid, which does not inhibit polyunsaturated fatty acid oxygenation pathways, yielded results identical to those of control larvae. Inhibition of eicosanoid formation with specific inhibitors of phospholipase $A_2$, cyclooxygenase and lipoxygenase significantly reduces the ability of larvae to clear pathogenic bacteria from their hemolymph. Inhibitors of eicosanoid biosynthesis inhibit the invertebrate immune response to bacterial infections.

EXAMPLE 2

Larval tobacco hornworms, M. sexta, were reared as described in Example 1. Larva were intrahemocoelically injected with 50 µg of dexamethasone, a phospholipase $A_2$ inhibitor, in 5 µl absolute ethanol. Three to ten minutes after injection of the inhibitors, larvae were infected with S. marcescens by intrahemocoelic injection of about $5 \times 10^5$ bacterial cells in 10 µl of broth, on the opposite side. Control larvae were injected with 5 µl of absolute ethanol and then similarly infected with bacteria. At 15 minutes intervals post-infection, 15 µl of hemolymph samples were serially withdrawn from the caudal horn, diluted and plated onto standard methods agar plates, and incubated for 36–40 hours. Bacterial colonies on each plate were then counted.

Within one hour post-infection, the dexamethasone-treated hornworms showed an increased in bacterial growth. At 15 minutes post-infection, $1.8 \times 10^4$ colony forming units (CFU) of bacteria per ml of hemolymph were detected, and by 45 minutes post-infection, that number had nearly doubled to $3.3 \times 10^4$ CFU/ml. By 60 minutes post-infection, bacteria in the dexamethasone-treated worms was increased 2.5 times that of the level of bacteria at 15 minutes post-infection. In contrast, bacteria recovery from control hornworms was below $10^3$ CFU for the first hour post-infection and no increase in growth of the bacteria was detected. These results indicate that inhibition of eicosanoid biosynthesis allowed bacterial growth to begin early in the hemolymph and inhibited early immune responses.

EXAMPLE 3

M. sexta larvae were intrahemocoelically injected with ethanol, or with different dosages of dexamethasone, including $1.4 \times 10^{-5}$ or $1.4 \times 10^{-3}$ or $1.4 \times 10^{-3}$ µg of dexamethasone per larvae, and then infected with $6 \times 10^5$ of S. marcescens. After a 1-hour incubation at 30° C., 100 µl of hemolymph was withdrawn from each insect as described in Example 1. The hemolymph was placed in 10 ml of dilution broth and 0.1 ml was plated in duplicate on standard methods agar. The plates were incubated, and bacterial colonies were counted as described in Example 1.

Hemolymph samples from larvae treated with ethanol or with a lower dose of $1.4 \times 10^{-5}$ µg of dexamethasone per larvae had a very low level of bacterial infection with $0.35 \times 10^4$ CFU for the control and $0.55 \times 10^4$ CFU for the $1.4 \times 10^{-5}$ µg of dexamethasone-treated larvae. Larvae treated with higher doses of $1.4 \times 10^{-3}$ µg or $1.4 \times 10^{-1}$ µg of dexamethasone had significantly increased levels of bacterial growth with $8.2 \times 10^4$ CFU and $10.1 \times 10^4$ CFU/ml of hemolymph, respectively. Other experiments with higher dosages of dexamethasone did not further increase recovery of bacterial colonies. Dexamethasone treatment compromised the ability of hornworm larvae to clear S. marcescens from hemolymph in a dose-responsive manner. As the dose of the inhibitor increased, an increase in bacterial growth was observed indicating an inhibition of the immune response.

EXAMPLE 4

M. sexta larvae were injected with $1.4 \times 10^{-5}$, $1.4 \times 10^{-3}$ or $1.4 \times 10^{-1}$ µg of dexamethasone per larvae, as in Example 3. M. sexta larvae were also injected with 0.14 µg of dexamethasone plus 50 µg of arachidonic acid. Control larvae received 5 µl of absolute ethanol. The larvae were then intrahemocoelically infected with $6 \times 10^5$ cells of the bacteria S. marcescens. After 14 hours at 30° C., surviving larvae were counted. Unchallenged larvae were injected with large doses of dexamethasone, ethanol, the cell free bacterial culture broth and arachidonic acid. In all cases unchallenged larvae survived during the 24 hour experimental period and showed no adverse behavioral effects.

The results of dexamethasone treatment on larval survival show that an increase in the dose of the inhibitor resulted in an increase in the mortality of the invertebrate species. At 14 hours post-infection, 46.3% of the ethanol treated control larvae, and 43.9% of the larvae treated with the low dose of $1.4 \times 10^{-5}$ µg of dexamethasone per larvae were alive. Larvae treated with higher doses of $1.4 \times 10^{-1}$ µg or $1.4 \times 10^{-3}$ µg of dexamethasone only 9.8% and 24.4% of the larvae were alive, respectively.

The higher concentrations of dexamethasone greatly reduced the proportion of larvae that survived pathogen S. marcescens infection. The effect of the higher concentrations of dexamethasone was reversed by treatment with arachidonic acid. At 14 hours post-infection, 45% of the larvae treated with both dexamethasone and arachidonic acid were alive when compared with 46.3% of the ethanol treated control larvae. In contrast, only 9.8% of the larvae treated with 0.14 µg of dexamethasone alone survived. Thus, dexamethasone and the other inhibitors of eicosanoid biosynthesis compromise the ability of the larvae to clear bacteria from circulation and increase mortality in the first 24 hours post-infection. This effect is reversed by the presence of arachidonic acid indicating that eicosanoids mediate important early steps in the immune response which affect the survivability of the organism.

EXAMPLE 5

Total lipids were extracted from hemolymph and fat bodies from five fifth-instar larvae. Phospholipids were further isolated by thin-layer chromatography of the total lipid extract. Purified phospholipids were transmethylated by refluxing in acidified methanol for 1 hour at 85° C. Resulting fatty acid methyl esters were analyzed by gas chromatography and mass spectrometry.

Analysis of the fatty acid compositions of phospholipids purified from hemolymph M. sexta larvae showed that all three eicosanoid precursor polyunsaturated fatty acids were present. These three components accounted for about 1% of the total phospholipid fatty acids, comparable to results from many other terrestrial insect species. The precursor polyunsaturated fatty acids were composed of 20%, 20:3 (n-6), 34% 20:4 (n-6) and 46% 20:5 (n-3). Retention times and mass spectra of these compounds were exactly congruent with authentic standards. Thus, all potential eicosanoid precursors were present in sufficient quantities to support eicosanoid biosynthesis.

EXAMPLE 6

Fifth instar M. sexta larvae were injected with $9.25 \times 10^5$ Bq of tritiated arachidonic acid ([5,6,8,9,11,12,14,15-$^3$H] 20:4; 2.22–3.70 TBq/mmol). After 1 minute, 100 µl of hemolymph was collected as described in Example 1. Eicosanoids were extracted three times with acidified ethyl acetate and then separated by thin-layer chromatography. Fractions were identified by cochromatography with authentic unlabeled standards and radioactivity in each fraction was assayed by liquid scintillation counting on a LKB-Wallac 1219 Rackbeta counter at 66% counting efficiency.

One minute after injection, 100 μl of hemolymph samples were withdrawn from each of seven larvae. In these samples, 5.3% of the injected radioactivity (mean=2.9×10$^5$ DPM) was recovered. Most (95 to 97%) of the recovered radioactivity was arachidonic acid. Three fractions had chromatographic behavior identical to the prostaglandins PGF$_2$α, each PGE$_2$ and PGD$_2$. A similar amount of radioactivity was also recovered in an otherwise uncharacterized fraction in the R$_f$ range reported for lipoxygenase metabolites in mammalian systems, presumably hydroxyeicosatetraenoic acids. Thus, larvae of *M. sexta* were able to convert radioactive arachidonic acid into eicosanoids.

EXAMPLE 7

Healthy penaeid shrimp held in aquaculture tanks are injected with either 1 μg/gm body weight of PGE$_2$, PGF$_{2α}$, PGD$_2$, arachidonic acid, hydroxyeicosatetraenoic acid, 15(R)-15 methyl-PGE2 (a PGE$_2$ analog) or dl-(11R,15RS)-11,15-dehydroxy-15-methyl-9-oxo-13-thioprostanoic acid, p-benzamidophenyl ester (a prostaglandin analog) in phosphate buffered saline. The shrimp are then injected with two-fold dilutions of *Vibrio parahemaelyticus* biotype *alginolyticus* or *Vibrio anquillarum* and observed for the development of clinical signs of bacterial infection and subsequent mortality. Clinical signs of bacterial infection include lethargy, white discoloration of abdominal musculature, dorsal flexure of the abdomen, redness of periopods and pleopods. The ability of prostaglandins and prostaglandin analogs to protect the shrimp from fatal bacteremia is examined. Protection of the shrimp from fetal bacteremia by treatment with a prostaglandin or its analogs is likely.

EXAMPLE 8

*Anopheles larvae* are treated with dexamethasone or dexamethasone and esculetin and/or the *Bacillus thurigiensis* serotype H-14. For field application against floodwater mosquitos, 500 grams of *Bacillus thurigiensis* wettable powder is suspended in 10 liters of phosphate buffered saline or phosphate buffered saline with 1 mg/ml dexamethasone or phosphate buffered saline with 1 mg/ml of dexamethasone and esculetin. The mixture is applied by pressurized sprayers on one ha of water surface. Some areas are treated with 1 mg/ml of dexamethasone in phosphate buffered saline alone or 1 mg/ml dexamethasone and 1 mg/ml esculetin of phosphate buffered saline. The effect of inhibitors of eicosanoid biosynthesis on mosquito growth is observed in the presence and absence of a known bio-control agent *Bacillus thurigiensis* serotype H-14. An increase in mortality associated with the infection of *Bacillus thurigiensis* in the presence of inhibitors of eicosanoid biosynthesis is likely.

What is claimed is:

1. A method of altering a cellular immune response of an arthropod comprising: administering a pharmaceutical composition to an arthropod in an effective amount to inhibit an eicosanoid-mediated cellular immune response of the arthropod, the composition comprising a biologically active agent which is effective to inhibit eicosanoid-mediated cellular immune responses of the arthropod and a physiologically acceptable carrier.

2. A method of claim 1, wherein the biologically active agent is an eicosanoid biosynthesis inhibitor selected from the group consisting of: cinnamic acid, glucocorticoids, dihydroxybenzopyran ketones, methanoleukotrienes, binaphthalenes, naphthalene acetic acids, phosphorylcholines, indole acetic acids, dihydropyridine carboxylic acids, phenanthrene carboxylic acids, salicylic acid, salicylic acid acetate, neomycins, benzoxazoleacetic acids, and dihydroxyanthrones.

3. A method of claim 1, wherein the biologically active agent is selected from the group consisting of: Ebselen (2-phenyl-1,2-benzisoselenazol-3(2H)-one), REV-5901 (2-[3(1-hydroxyhexyl)phenoxymethyl]quinoline hydrochloride), REV-5901 paraisomer, cinnamyl-3,4-dihydroxyl-a-cyano-cinnamate (CDC), Baicalein (5,6,7-trihydroxyflavone), caffeic acid, curcumin, CDP-choline, 5,6-dehydro-arachidonic acid, dexamethasone, DEDA (7,7-dimethyl-eicosadienoic acid), dipyridamole, ETYA (5,8,11, 14-eicosatetraynoic acid), ETI (5,8,11-eicosatriynoic acid), esculetin, gossypol, indomethacin, 5,6-methanoleukotriene A$_4$ methyl ester, naproxen, NDGA (nordihydroguaiaretic acid), oleyloxyethyl phosphorylcholine, phenidone, chlorpromazine HCl, manoalide, nifedipine, aminocephalosporanic acid, aristolochic acid, Compound 48/80, neomycin sulfate, aspirin, benoxaprofen, AA-861 (2-(12-hydroxy-5, 10-dodecadiynyl)-3,5,6-trimethyl-p-benzoquinone), nafazatrom, quericetrin, REV-5367, REV-5741, REV-5747, REV-5827, REV-5875, REV-5965, REV-6080, anthralin, cyclooxygenase inhibitors, 5-lipoxygenase inhibitors, 12-lipoxygenase inhibitors, and phospholipase inhibitors.

4. A method of claim 1, wherein the biologically active agent is selected from the group consisting of: 13-APA (13-azaprostanoic acid), carbacyclin, CTA$_2$ (carbocyclic thromboxane A2), U-44069 (9,11-dideoxy-11-α-9-α-epoxymethanoprostaglandin F2α), U-46619 ((15S)-15-hydroxy-11-α-9-α-(epoxymethano)prosta-5(Z),13(E)-dienoic acid), DSCG (cromolyn), oxatomide, PTA$_2$, (pinane thromboxane A2), and xanthines.

5. A method according to claim 1, wherein the composition further comprises a surface active agent.

6. A method according to claim 1, wherein administering the composition comprises spraying the composition onto the arthropod.

7. A method according to claim 1, wherein administering the composition comprises injecting the composition into the arthropod.

8. A method according to claim 1, wherein administering the composition comprises feeding the composition to the arthropod.

9. A method of decreasing cellular immunity of an arthropod to disease, comprising administering to the arthropod a biopesticide composition in an effective amount to decrease a cellular immune response, the composition comprising a biologically active agent which inhibits eicosanoid-mediated cellular immune responses and a physiologically acceptable carrier.

10. A method of claim 9, wherein the biologically active agent is selected from the group consisting of: cinnamic acid, glucocorticoids, dihydroxybenzopyran ketones, methanoleukotrienes, binaphthalenes, naphthalene acetic acids, phosphorylcholines, indole acetic acids, dihydropyridine carboxylic acids, phenanthrene carboxylic acids, salicylic acid, salicylic acid acetate, neomycins, benzoxazoleacetic acids, and dihydroxyanthrones.

11. A method of claim 9, wherein the biologically active agent is selected from the group consisting of: Ebselen (2-phenyl-1,2-benzisoselenazol-3(2H)-one), REV-5901 (2-[3(1-hydroxyhexyl)phenoxymethyl]quinoline hydrochloride), REV-5901 paraisomer, cinnamyl-3,4-dihydroxyl-a-cyano-cinnamate (CDC), Baicalein (5,6,7-trihydroxyflavone), caffeic acid, curcumin, CDP-choline, 5,6-dehydro-arachidonic acid, dexamethasone, DEDA (7,7-dimethyl-eicosadienoic acid), dipyridamole, ETYA (5,8,11, 14-eicosatetraynoic acid), ETI (5,8,11-eicosatriynoic acid), esculetin, gossypol, indomethacin, 5,6-methanoleukotriene $A_4$ methyl ester, naproxen, NDGA (nordihydroguaiaretic acid), oleyloxyethyl phosphorylcholine, phenidone, chlorpromazine HCl, manoalide, nifedipine, aminocephalosporanic acid, aristolochic acid, Compound 48/80, neomycin sulfate, aspirin, benoxaprofen, AA-861 (2-(12-hydroxy-5,10-dodecadiynyl)-3,5,6-trimethyl-p-benzoquinone), nafazatrom, quericetrin, REV-5367, REV-5741, REV-5747, REV-5827, REV-5875, REV-5965, REV-6080, anthralin, cyclooxygenase inhibitors, 5-lipoxygenase inhibitors, 12-lipoxygenase inhibitors, and phospholipase inhibitors.

12. A method of claim 9, wherein the biologically active agent is selected from the group consisting of: 13-APA (13-azaprostanoic acid), carbacyclin, $CTA_2$ (carbocyclic thromboxane A2), U-44069 (9,11-dideoxy-11-α-9-α-epoxymethanoprostaglandin F2α), U-46619 ((15S)-15-hydroxy-11-α-9-α-(epoxymethano)prosta-5(Z),13(E)-dienoic acid), DSCG (cromolyn), oxatomide, $PTA_2$, (pinane thromboxane A2), and xanthines.

* * * * *

UNITED STATES PATENT AND TRADEMARK OFFICE
CERTIFICATE OF CORRECTION

PATENT NO.         : 6,099,834
APPLICATION NO. : 08/912455
DATED                 : August 8, 2000
INVENTOR(S)       : Stanley It is certified that error appears in the above-identified patent and that said Letters Patent is hereby corrected as shown below:

Col. 1 lines 3-4 should read,
Rights in the United States Government

This invention was made with federal support under the following research grant: 58-5430-5-0115 awarded by the USDA. The United States government has certain rights to this invention.

Signed and Sealed this

Twenty-fourth Day of February, 2009

JOHN DOLL
*Acting Director of the United States Patent and Trademark Office*